(12) United States Patent
Martens

(10) Patent No.: US 6,510,201 B2
(45) Date of Patent: Jan. 21, 2003

(54) APPARATUS FOR MEASURING THE PULSE TRANSMISSION SPECTRUM OF ELASTICALLY SCATTERED X-RAY QUANTITIES

(75) Inventor: Gerhard Martens, Henstedt-Ulzburg (DE)

(73) Assignee: YXLON International X-Ray GmbH, Hamburg (DE)

( * ) Notice: Subject to any disclaimer, the term of this patent is extended or adjusted under 35 U.S.C. 154(b) by 0 days.

(21) Appl. No.: 10/047,970

(22) Filed: Jan. 16, 2002

(65) Prior Publication Data

US 2002/0094061 A1 Jul. 18, 2002

(30) Foreign Application Priority Data

Jan. 17, 2001 (EP) .............................. 01100950

(51) Int. Cl.[7] ............................................ G01N 23/201
(52) U.S. Cl. .............................. 378/86; 378/87; 378/88; 250/363.03
(58) Field of Search .......................... 378/86, 87, 88, 378/89, 145, 147, 149; 250/363.03

(56) References Cited

U.S. PATENT DOCUMENTS

| | | | | |
|---|---|---|---|---|
| 5,231,652 A | * | 7/1993 | Harding | 378/147 |
| 5,265,144 A | | 11/1993 | Harding et al. | |
| 5,602,893 A | * | 2/1997 | Harding | 378/147 |
| 6,054,712 A | * | 4/2000 | Komardin et al. | 250/363.06 |
| 6,175,117 B1 | * | 1/2001 | Komardin et al. | 250/363.06 |

FOREIGN PATENT DOCUMENTS

| | | |
|---|---|---|
| DE | 4222227 | 1/1994 |
| DE | 4445876 | 6/1996 |

* cited by examiner

Primary Examiner—David V. Bruce
Assistant Examiner—Pamela R. Hobden
(74) Attorney, Agent, or Firm—Friedrich Kueffner

(57) ABSTRACT

An apparatus for measuring the pulse transmission spectrum of elastically scattered quantities includes at least one diaphragm displaceable in a y-direction for switching between fine and coarse local resolution of the examined partial volumes of an examination object, wherein the diaphragm narrows the effective ray width transversely of a scanning direction, and a diaphragm system displaceable in a x-direction for limiting and extension of the partial volume in a z-direction, wherein the diaphragm system includes at least two circular ring diaphragms arranged one above the other and identical with respect to their circular ring structure, and wherein the circular ring diaphragms are arranged at a relative offset for reducing an effective imaging slot width or a detector slot width.

5 Claims, 16 Drawing Sheets

Basic Diaphragm (Fixed Diaphragm)

Displaceable Diaphragm

APPARATUS FOR MEASURING THE PULSE TRANSMISSION SPECTRUM OF ELASTICALLY SCATTERED X-RAY QUANTITIES

BACKGROUND OF THE INVENTION

1. Field of the Invention

The present invention relates to an apparatus for measuring the pulse transmission spectrum of elastically scattered X-ray quantities.

2. Description of the Related Art

An apparatus of the above-described type has been disclosed in DE-A-42 22 227 and EP-B1-0 496 454. The teachings of these references introduce examination or detection systems for large objects which are based on the detection of the elastic scattering of x-rays. The elastically scattered x-ray radiation exhibits in its energy spectrum characteristic structures which makes it possible to make conclusions concerning the type of the scattering material. For example, it is possible to identify materials such as explosives or drugs in containers such as travel luggage, packages, letters, or the like (H. Strecker; Automatische Gepäckkontrolle mit Röntgenstreustrahlung; [Automatic luggage control using x-ray radiation] Physik in unserer Zeit 30, 31–34 (1999).

The principal difference of the two scattered ray systems described above resides in the use of different geometric configurations which are utilized for radiating the examined object. In DE-A-42 22 227, a cone-shaped ray bundle is used for radiation, as it is illustrated in FIG. 1 with an exaggerated aperture angle. The primary ray bundle is masked from the x-ray lobe which leaves the x-ray focus by an appropriate annular diaphragm. The diameter of the primary ray cone in the object space initially determines the horizontal spatial local resolution. The resolution is in the order of magnitude of several cm and can be varied only insignificantly by the choice of the primary cone aperture angle and the distance of the primary collimator diaphragm from the focus because these two variables are significantly limited by other system parameters.

Examined objects which are located in the object space partially scatter the primary x-ray light (see the right side of FIG. 1). Portions of this scattered light are directed to a circular ring-shaped segmented detector through a secondary collimator which is essentially composed of a circular ring-shaped imaging or focusing diaphragm system and a detector diaphragm system. By using several slot systems arranged next to each other it is possible to divide the entire object space vertically into several partially overlapping image layers. For example, FIG. 2 shows how two image layers located one above the other can be focused through an imaging slot onto two detector elements.

Horizontal scanning of the examined object takes place by a meander-like displacement of the x-ray and detector system and the examined object with a timed detection of the x-ray signals in the detector.

The spatial resolution of the examined partial volumes (voxels) of the object space depends

- in x-direction on the relative displacement speed, the integration time intervals and the diameter of the primary x-ray cone,
- in y-direction on the diameter of the primary x-ray cone,
- in z-direction on the slot width of all involved slot diaphragms.

A first attempt for reducing the resolution can be found in DE-A-44 45 876 in which semicircular diaphragm structures and a semicircular structured detector are used. The left and right diaphragm system are arranged displaced relative to each other in such a way that the resulting imaging layers from the left and right system halves are vertically nested into one another and overlap each other partially.

The resolution in the x-direction now only depends on the relative displacement speed and the integration time intervals.

In contrast to DE-A-42 22 227, EP-B1 0496454 utilizes a pin ray for radiating the examined object. A principal sketch for this system is shown in FIG. 3. The needle ray is masked from the x-ray lobe leaving the x-ray focus by means of a small pin diaphragm having a diameter of about 1 mm. Since the divergence of the pin ray is very small, its diameter in the object space is also only about 1 mm.

Consequently, the lateral resolution of the partial volumes (voxels) of the pin ray system is

- very fine in the y-direction
- adjustable in the x-direction by the relative displacement speed and the integration time intervals,
- dependent in the z-direction on the slot width of all involved slot diaphragms.

The necessity of adjusting the local resolution to the examined object is a consequence of the type of examination to be performed. For example, the scattered ray geometry used for examining containers for different materials, such as travel luggage with explosives or drugs in minimum quantities of several 100 g is significantly different from the examination of briefcases, packages and letters for significantly smaller quantities of explosives or drugs in the range of a few 10 g. Consequently, it is desirable to have a scattered x-ray system available which is capable simultaneously to detect large and small quantities of substances. It is understood that an easy and quick manipulation of the apparatus should be possible.

SUMMARY OF THE INVENTION

Therefore, it is the primary object of the present invention to improve the apparatus described above in such a way that it can be adapted to the respective object to be examined and its contents. The apparatus should make it possible, for example, after a coarse scan of a container, such as a piece of luggage or the like, in suspicious cases to once again locally examine the critical areas with a finer resolution or, if there is already an initial suspicion, to carry out a full scan with high local resolution, i.e., with high sensitivity for small quantities.

In accordance with the present invention, the arrangement for measuring the pulse transmission spectrum of elastically scattered x-ray quantities of the above-described type includes

- a polychromatic x-ray emitter;
- a primary diaphragm arrangement arranged between the x-ray emitter and an examination area through which the x-ray radiation is conducted, wherein the primary diaphragm arrangement serves to mask a primary ray bundle or pin ray bundle extending through the examination area on the surface of a cone;
- a detector arrangement composed of several detector elements concentrically surrounding the detector center point for determining the x-ray quantities scattered in the examination area;
- a secondary diaphragm arrangement arranged between the examination area and the detector arrangement, wherein the secondary diaphragm arrangement includes at least one imaging slot for imaging the scattered x-ray radiation on the detector arrangement;

a device for the relative displacement between an examination object placed in the examination area and the examination arrangement for scanning the examination object in a scanning direction; and means for processing the measured signals, wherein the detector arrangement is divided by means of separating areas arranged perpendicularly of the scanning direction into a least two detector areas having essentially the same width, and wherein each detector area has a number of partial ring-shaped detector elements, and each detector element is provided with means for signal processing.

According to the present invention, the arrangement described above further includes a) at least one diaphragm displaceable in the y-direction for switching between fine and coarse local resolution of the examined partial volumes of the examination object, wherein the diaphragm narrows the effective ray width transversely of the scanning direction, and b) a diaphragm system displaceable in the x-direction for limiting the z-extension of the partial volumes, wherein the diaphragm system includes at least two circular ring diaphragms which are arranged one above the other and are identical with respect to their circular ring structure, wherein the circular ring diaphragms are arranged at a relative offset for reducing the effective imaging slot width or the detector slot width.

Accordingly, the present invention provides an arrangement in which the local resolution can be quickly switched by means of slidable diaphragms. The mechanical switching by means of diaphragms is provided for the y-direction and the z-direction of the local resolution.

The improvement of the local resolution $\Delta x=V^*\Delta t$ in the x-direction takes place by a reduction of the relative speed V or/and a shortening of the integration time $\Delta t$. FIG. 4a shows the resulting cross-sections of a voxel sequence for the case of a cone-shaped ray system with semicircular ring detector elements with a long measuring time $\Delta t_g$ and/or a high relative speed $V_g$, while FIG. 4b shows the sequence of the voxel cross-sections for short measuring times $\Delta t_k$ and/or low speeds $V_k$.

The improvement of the local resolution in the y-direction takes place by a displaceable diaphragm or pair of diaphragms extending into the x-ray bundle. It is almost entirely insignificant whether the primary ray cone is already limited by an additional diaphragm pair (y-diaphragm pair) in or below the primary collimator in its diameter in the y-direction, or whether the width of the scattered light bundle is narrowed immediately above the secondary collimator, in the secondary collimator or underneath the secondary collimator directly in front of the detector through a y-diaphragm pair. Preferred embodiments are shown in FIG. 5a for the y-diaphragm pair on the primary side and in FIG. 5b for the y-diaphragm pair on the secondary side. The result of the narrowing of the cross-section of the primary or secondary x-ray bundle is shown in FIG. 4c. FIG. 4c shows the row of narrowed voxel cross-sections arranged successively in the y-direction. The use of the plate-shaped pair of y-diaphragms requires a relatively long opposite movement of the two components, as well as a certain space requirement outside of the circular diaphragms, if the path of the rays is not to be narrowed; therefore, the partial y-diaphragm shown in FIGS. 5c and 5d is preferred.

The slidable diaphragms or diaphragm systems have the purpose to narrow or limit the z-extension of the voxels. This applies equally to voxels resulting from a cone-shaped ray and to the voxels of a pin ray system.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 12a is schematic illustration of the interaction of the first slidable diaphragm shown in FIG. 11b with the basic diaphragm shown in FIG. 11a;

FIG. 12b is a schematic illustration of the interaction of the first basic diaphragm shown in FIG. 11b with the remaining two slidable diaphragms of the type shown in FIG. 11b of the pin ray system;

DESCRIPTION OF THE PREFERRED EMBODIMENTS

Diaphragm system for vertically limiting the "conical surface" voxel:

The single-piece y-diaphragm has a complicated configuration and is composed essentially of three portions. In the inactive state shown in FIG. 5c, a diaphragm portion is located outside of the circular ring slot system to be partially covered and another portion is located within the circular ring system. The third portion is a mechanical connecting piece which rigidly couples the two outer portions of the y-diaphragm to each other. In the illustrated embodiment, the connecting portion is constructed as a simple rod or plate, however, it may also have a different shape as required.

Figure 5:
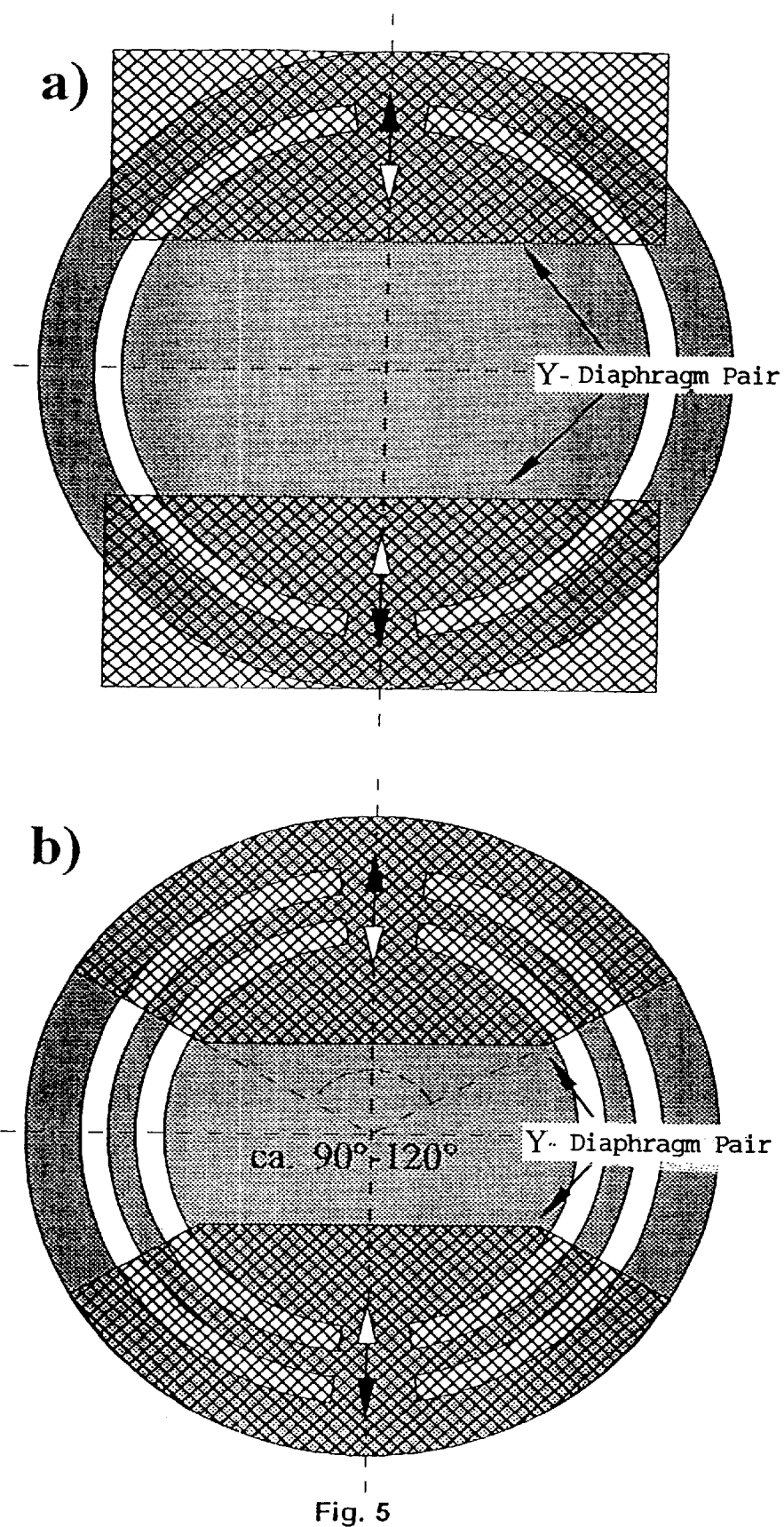
FIG. 5a shows the shape of the y-diaphragm used according to the present invention for narrowing the x-ray light bundle on the primary side in the transverse direction.
FIG. 5b shows the shape of the y-diaphragm used according to the present invention for narrowing the scattered x-ray light bundle on the secondary side in the transverse direction.
FIG. 5c is a schematic illustration of the shape of a single-piece y-diaphragm in the inactive state.
FIG. 5d is a schematic illustration of the shape of the y-diaphragm shown in FIG. 5c in the active state.
Figure 5:
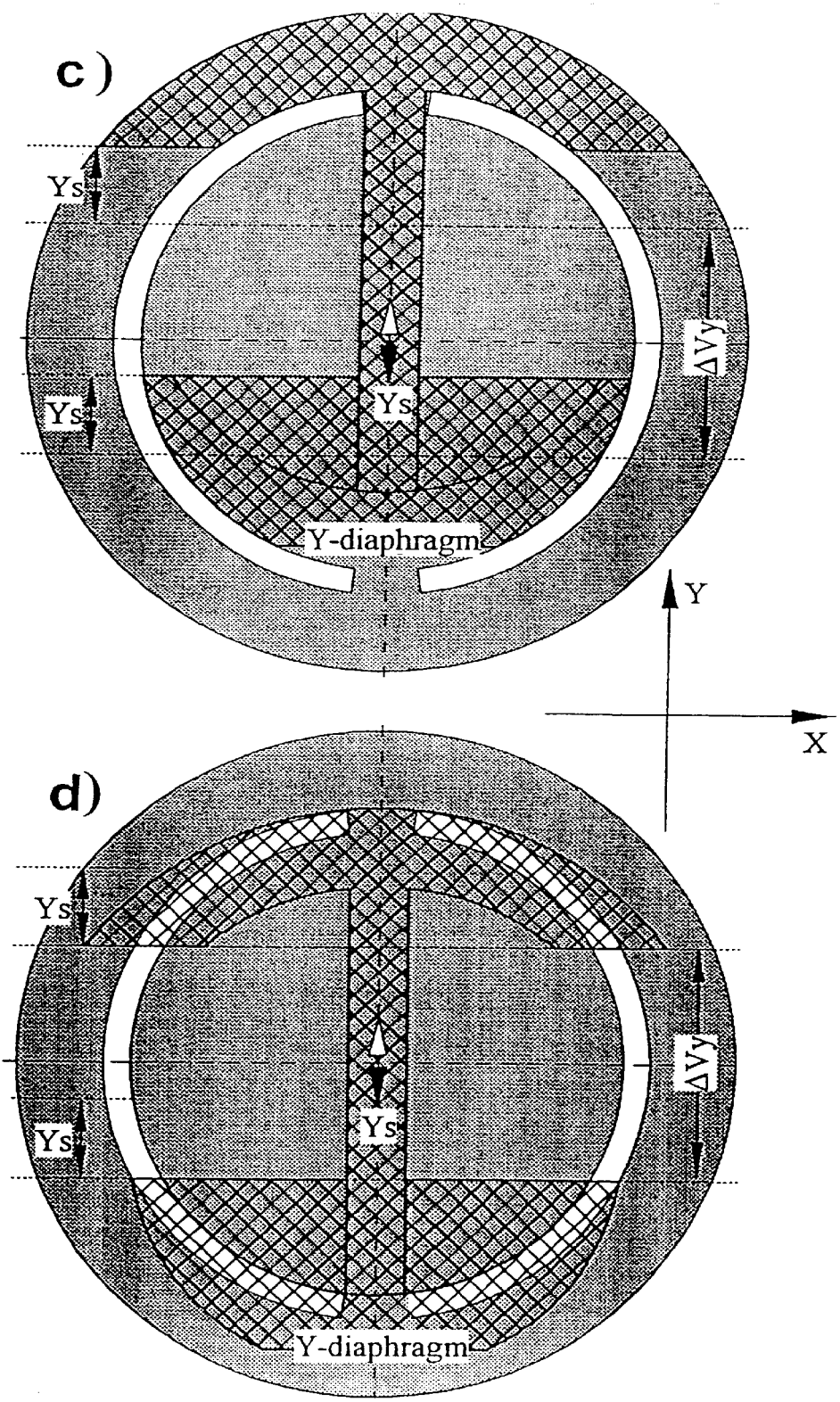

On the one hand, a displacement of the diaphragm in minus y-direction has the result that the portion of the y-diaphragm located outside of the circular ring slot moves inwardly and partially covers the circular ring slot. On the other hand, the portion of the y-diaphragm located in the inner circle of the circular ring slot system travels outwardly and simultaneously covers the opposite portion of the circular ring slot system. This results in the intended narrowing of the width of the circular ring slot system in the y-direction, as seen in FIG. 5d.

Figure 1:
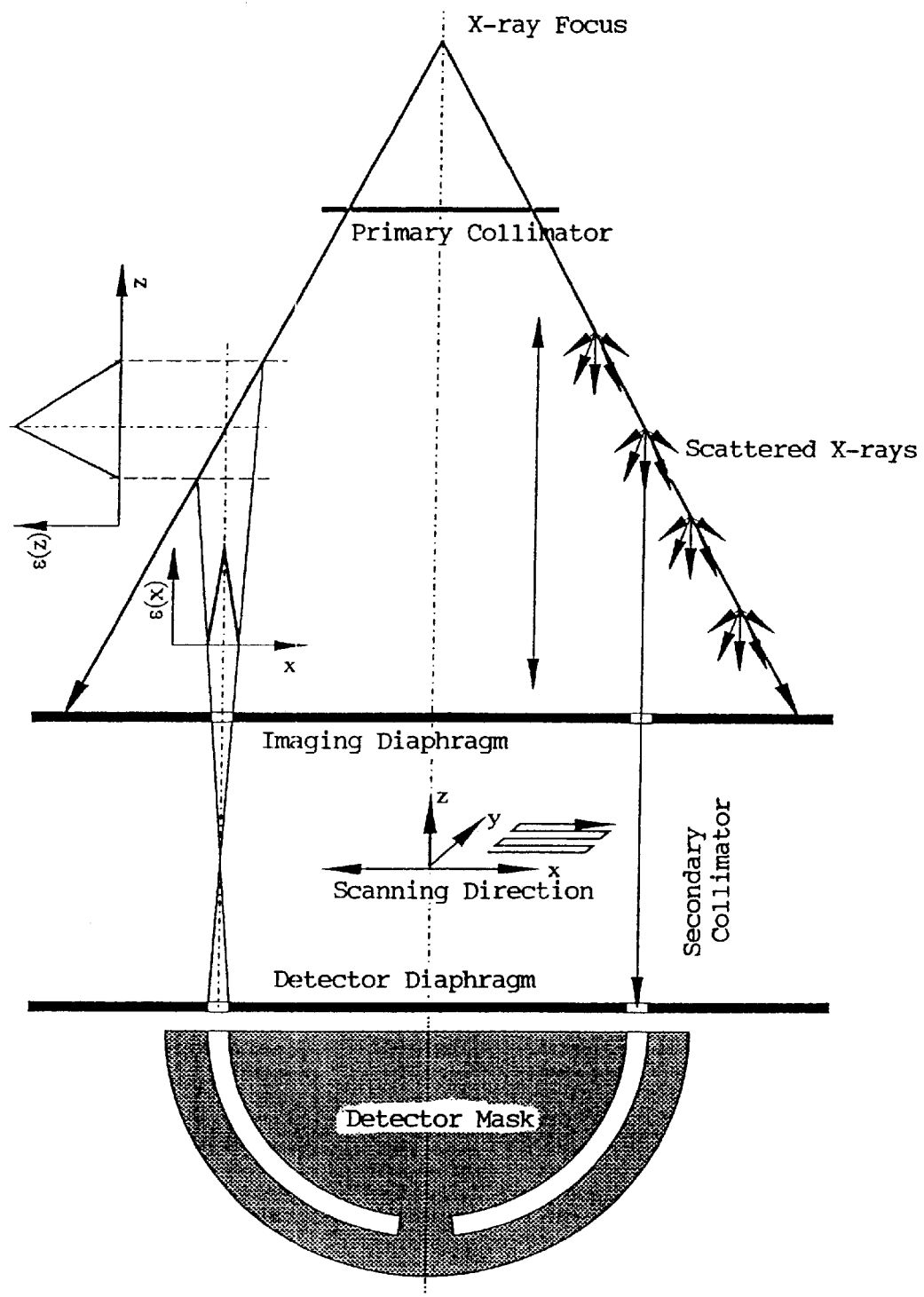
FIG. 1 is a schematic illustration of the principle of the scattered x-ray image with cone-shaped primary ray bundle and a highly exaggerated aperture angle according to the prior art.
Figure 2:
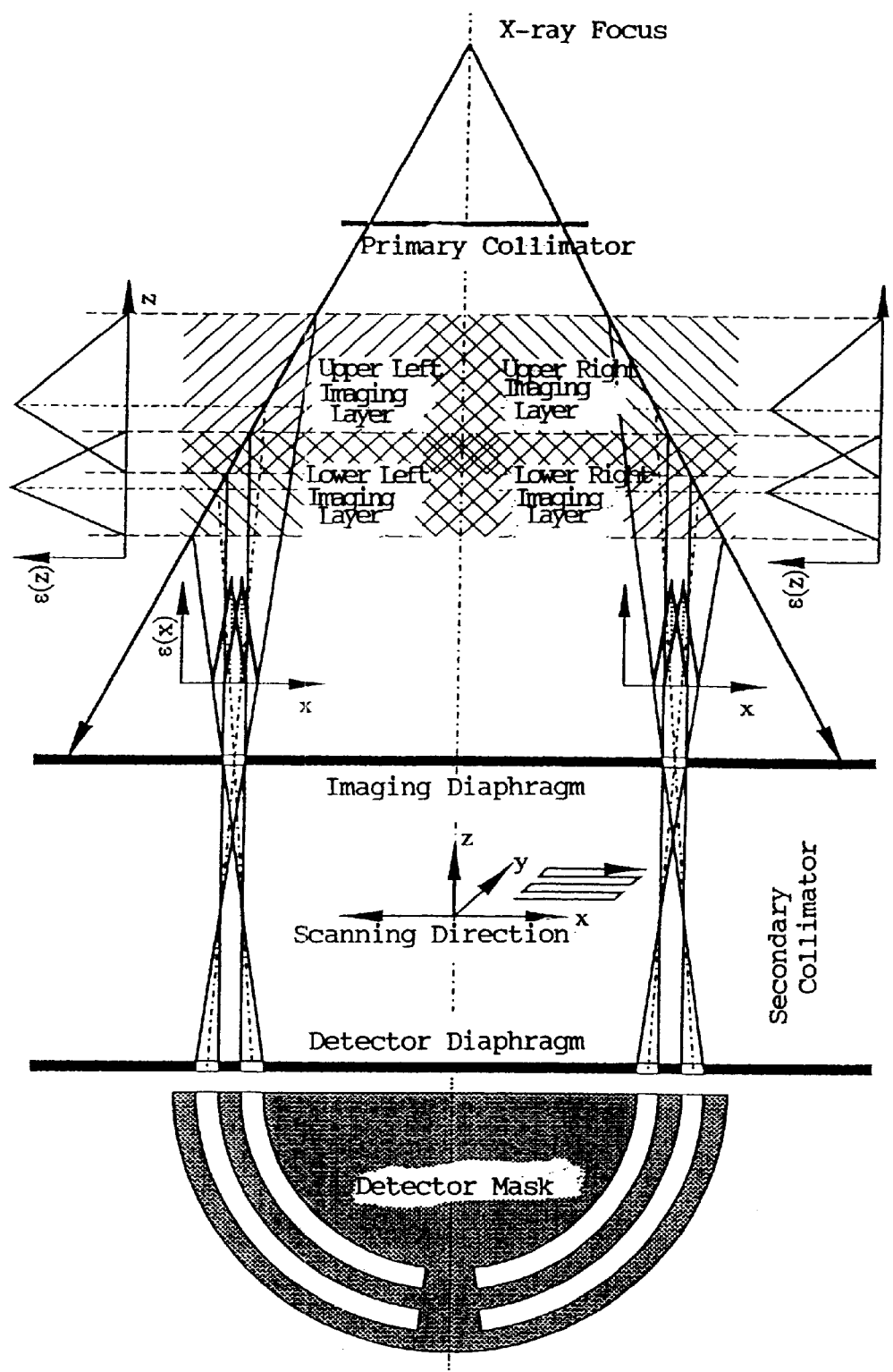
FIG. 2 is a schematic illustration of an example of the layer by layer filling of the examination space with multiple slot systems in the secondary collimator according to the prior art.
Figure 6:
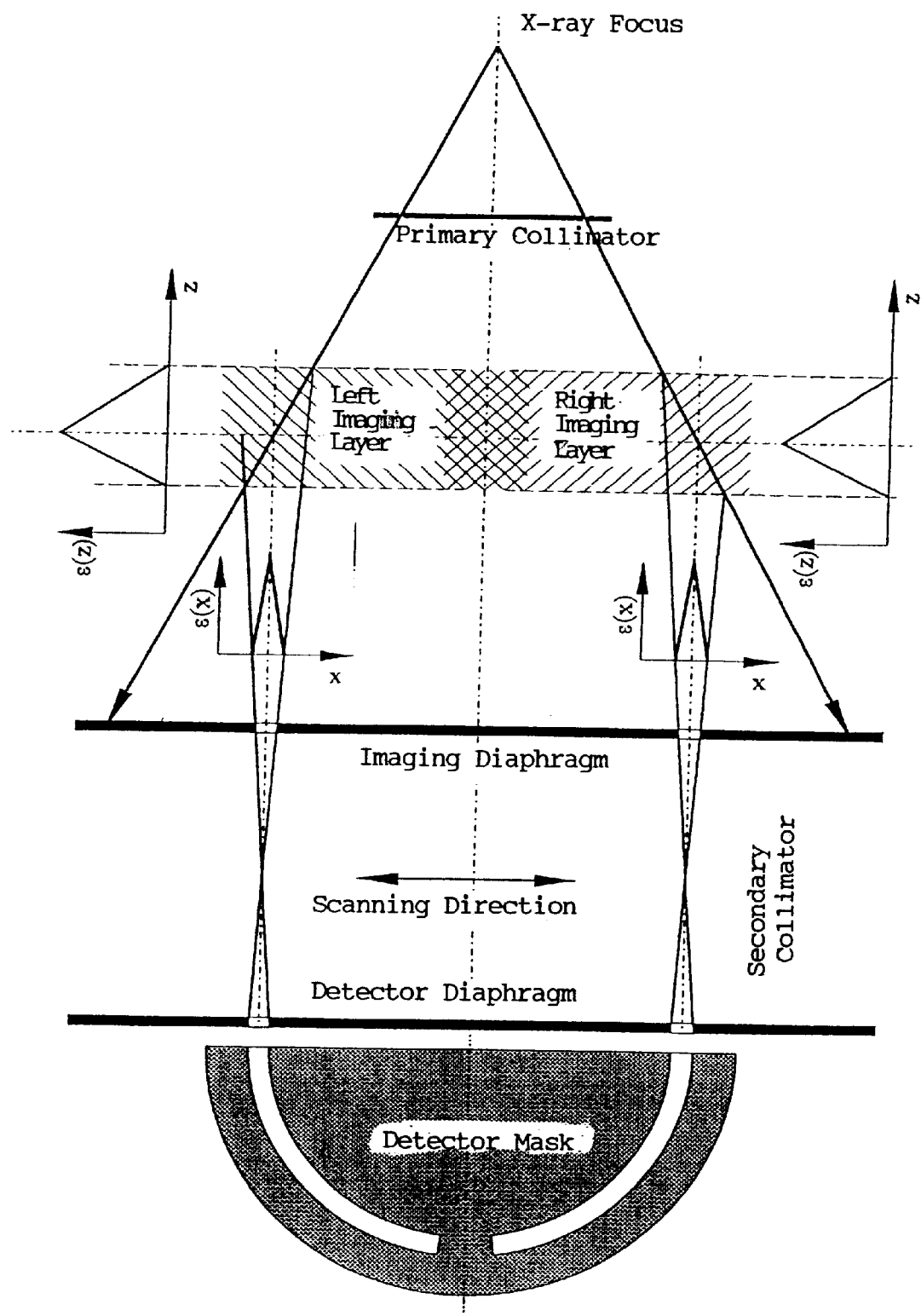
FIG. 6 is a schematic illustration of the symmetrical configuration of a scattered x-ray imaging system according to the present invention with semicircular detector and the same vertical position of the imaging layers.

The manner of operation of the diaphragms according to the invention for vertically narrowing the imaging layers will be described in connection with FIG. 6. FIG. 6 constitutes a completion of FIG. 1 and shows for a symmetrical semicircular ring detector mask the imaging layer arrangement for the left and right sides of the total system. For simplicity's sake, only two semicircular detector elements are shown which complement each other to form almost a circular ring. The semicircular ring detector elements look each through the detector diaphragm and the imaging diaphragm into the examination space. The intersections of the line of sight areas of the detector with the primary cone-shaped ray bundle result in the vertical positions of the respective imaging layers. However, the voxels scanned during the scanning process are laterally offset in the x-direction this must be adequately taken into consideration when the data are processed.

FIG. 6 additionally shows the so called intensity and sensitivity profiles $\epsilon(x)$ and $\epsilon(z)$. In a coarse approximation, these profiles are triangles and are shown as such in the drawing. The vertical positions of the left and right sensitivity profiles of the imaging layers coincide. In systems for large voxels, this fact can be utilized for adequately adding the signals of the left and right side in order to double the signal yield in this manner. Consequently, scanning can be carried out more quickly.

As can be seen in FIG. 6, the width of the sensitivity profiles (half-value widths or absolute base widths) depend on the slot width of the imaging diaphragm and the detector diaphragm. Consequently, the arrangement according to the present invention starts by dynamically reducing the slot width of the imaging diaphragm or the slot width of the detector diaphragm or the width of both diaphragms in order to reduce the vertical voxel extension.

One possibility for performing this reduction is to move by means of a motor another secondary collimator with smaller slot diaphragms into the place of the previous secondary collimator. However, because of the great masses and the required precision and the limited space in the scanner, this is a very complicated and expensive procedure. This is also true for a complete exchange by means of a motor of the imagining diaphragm, the detector diaphragm or both diaphragms against a diaphragm having smaller slot widths.

Figure 7:
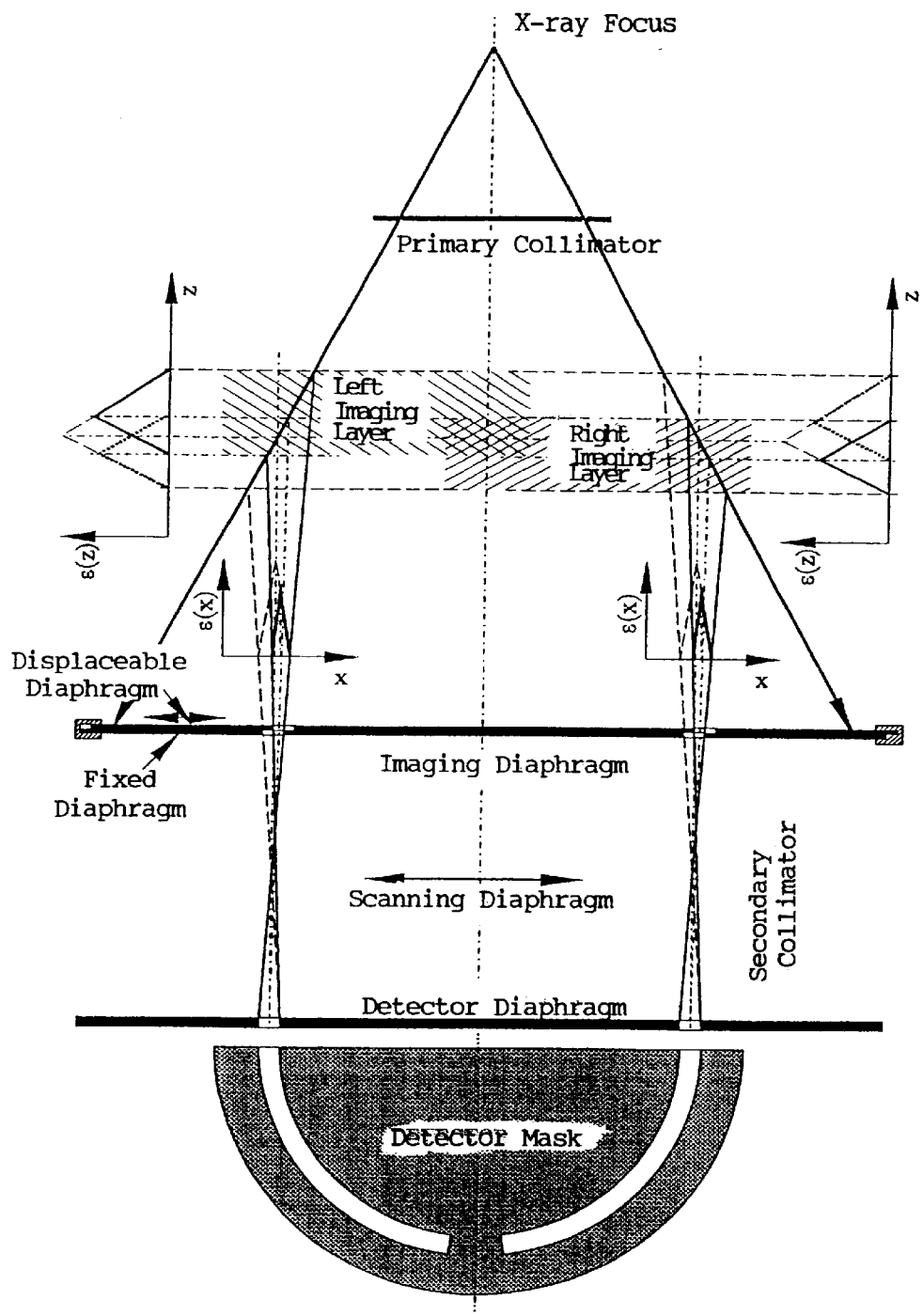
FIG. 7 is a schematic illustration of the arrangement of a scattered x-ray imaging system according to the present invention with a double imaging diaphragm and transverse offset of the upper diaphragm.

In accordance with the present invention, on the other hand, the effective slot widths are reduced directly. For this purpose, for example, the imaging diaphragm is replaced by two diaphragms preferably having half the thickness, wherein, however, both diaphragms have the same circular slot diaphragm structure. One of these diaphragms, for example, the lower diaphragm, is fixedly mounted. The second diaphragm is displaceable and is arranged, for example, directly above the first diaphragm. When the positions of the two diaphragms coincide, there is no change relative to the situation shown in FIG. 6 with respect to the equality of the layer positions of the left and right system halves. However, as soon as the moveable diaphragm is only slightly moved toward the right as seen in the drawing, preferably by half a slot width, two effects are obtained. As schematically shown in FIG. 7, the imaging layers become narrower and their vertical positions change. The imaging layer of the right system half is displaced downwardly and the imaging layer of the left system half is displaced upwardly. However, both imaging layers still overlap to a sufficient extent.

The displacement of the diaphragms can be carried out by means of electromagnets because the distances to be travelled are only within the range of a few 10th of a mm.

Figure 8:
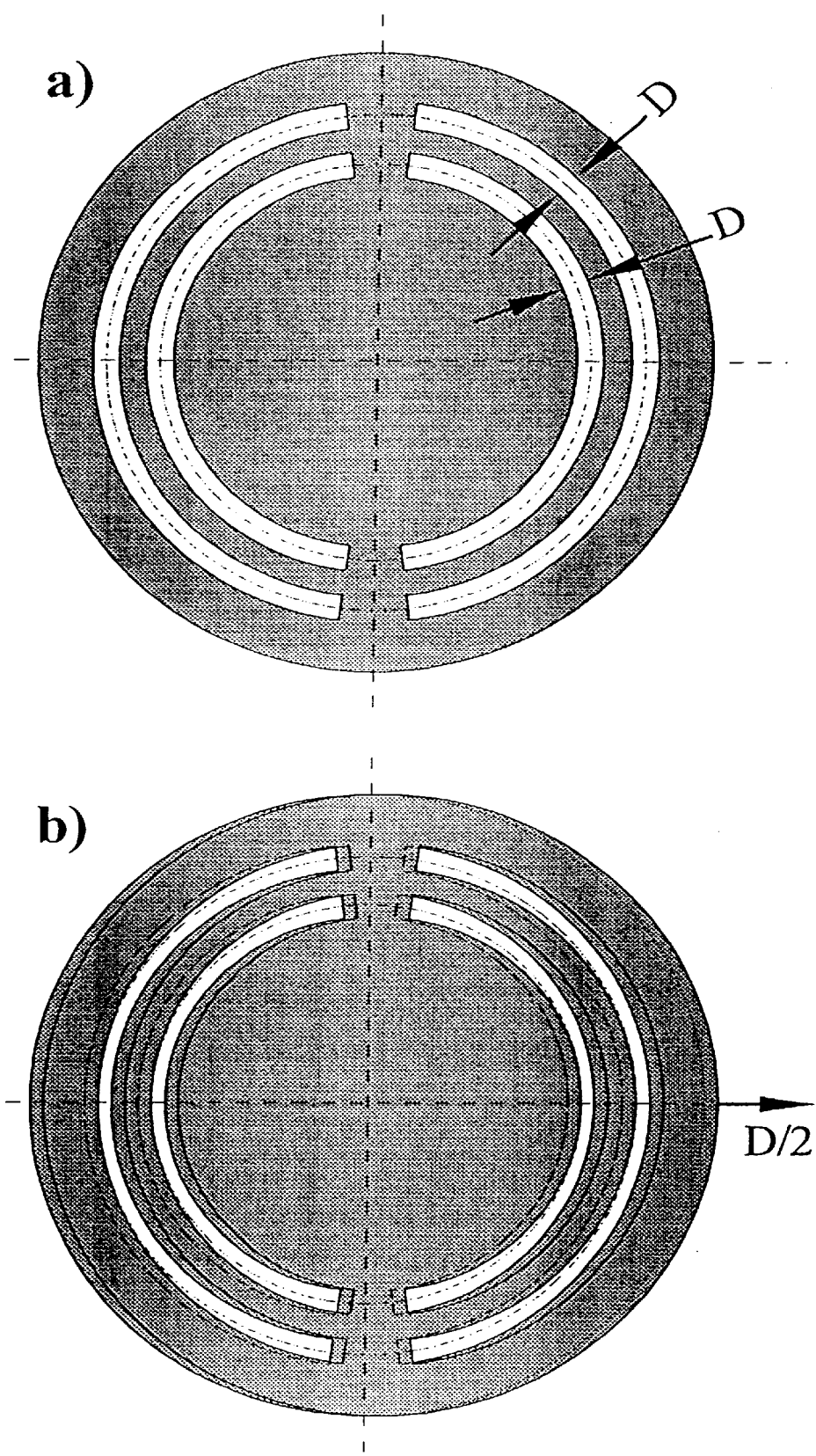
FIG. 8a is a schematic illustration of a pair of diaphragms used according to the present invention in the form of a double ring diaphragm with diaphragms arranged one above the other, wherein the diaphragms are not offset relative to each other.
FIG. 8b is a schematic illustration of a pair of diaphragms used according to the present invention in the form of a double ring diaphragm with diaphragms arranged one above the other, wherein the diaphragms are offset relative to each other by half a slot width.

FIG. 8 shows the effect of the diaphragm displacement in a top view of the pair of imaging diaphragms in the case of a double slot system. When the diaphragms are placed so as to coincide directly with each other, a semicircular ring system with uniform slot width D is obtained. However, if one of these diaphragms is displaced toward the right, for example, by D/2, only the right half of the slots remains open on the left and the right sides in the vicinity of the horizontal diameter (the diameter extending in the plane of the drawing from the left to the right). The left halves are covered.

Figure 9:
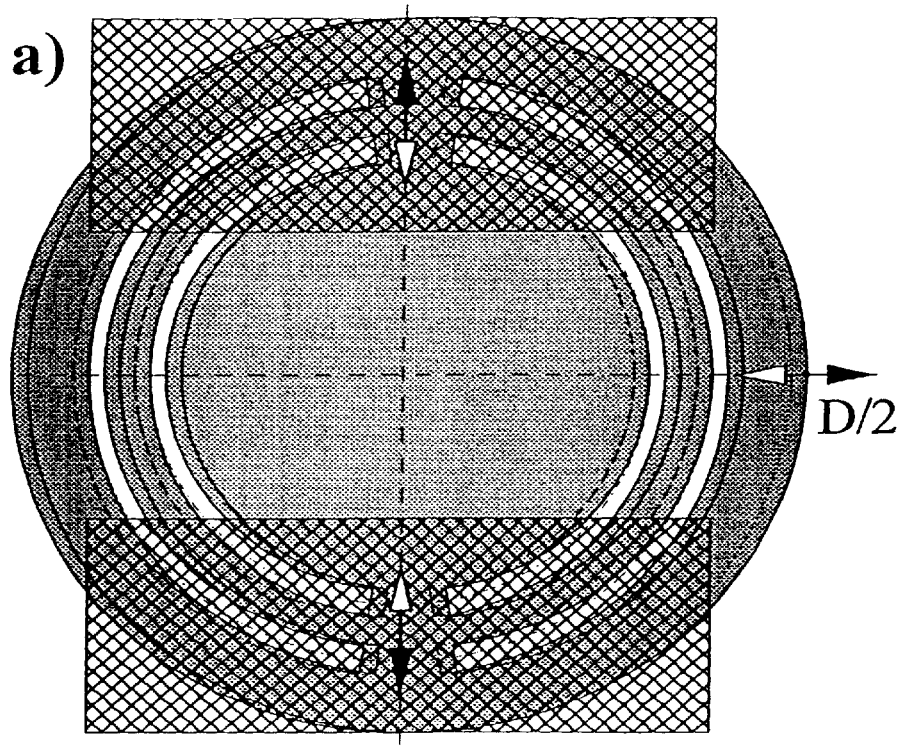
FIG. 9a and FIG. 9b are schematic illustrations showing covering of the non-optimum diaphragm portions by the y-diaphragm pair used according to the present invention.
Figure 9:
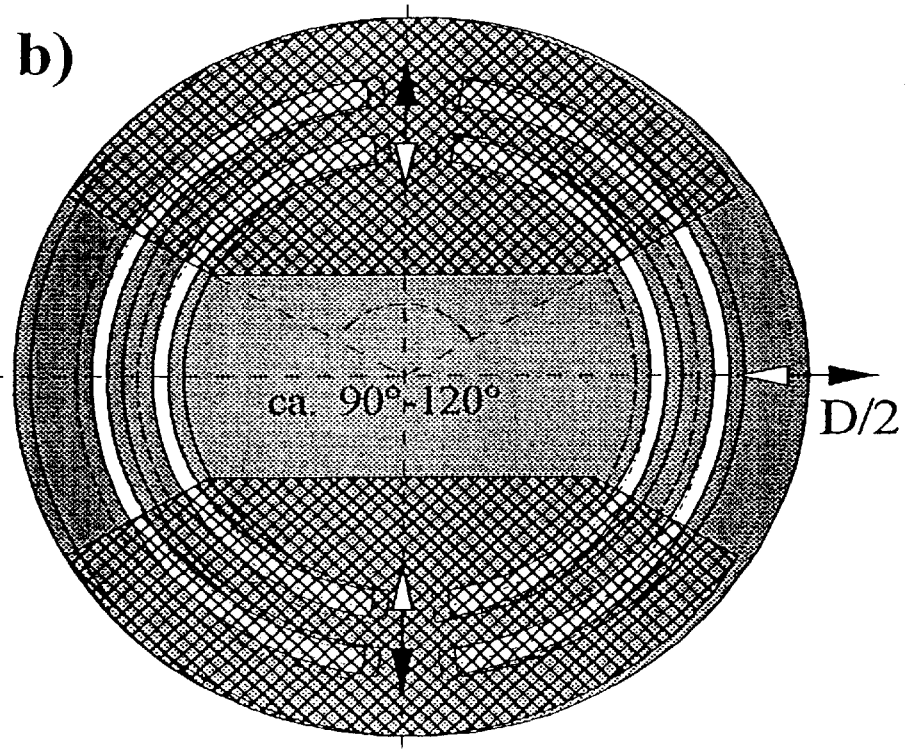

The slot widths toward the bottom and the top remain the same as before in the vicinity of the vertical diameter (the diameter extending from bottom to top in the plane of the drawing). However, these areas are already covered to a sufficient extent by the y-diaphragm pair discussed above for the voxel reduction in the y-direction, so that for the actually effective slots only about the desired half slot width is operational, as seen in FIG. 9.

However, it has been found that the vertical voxel displacement and the voxel reduction size by the displacement of the upper portion of the imaging diaphragm does not take place uniformly over the examination space for all imaging layers. The upper imaging layers have a significantly greater relative vertical displacement as compared to the lower layers. This problem can be eliminated by taking into consideration the finite extension of the primary ray bundle and its effect on the voxel size. Therefore, in accordance with the present invention, the circular ring diaphragm of the primary collimator is also constructed as a pair of diaphragms which are arranged directly one above the other and are congruent with respect to their ring structure. A displacement of the lower part of the diaphragm of the primary collimator diaphragm pair toward the left has the effect that the partial voxels of the right side of the system are moved downwardly and the left partial voxels of the system are moved upwardly. In this connection, it has been found that the lower imaging layers are moved to a greater extent than the upper layers.

Figure 10:
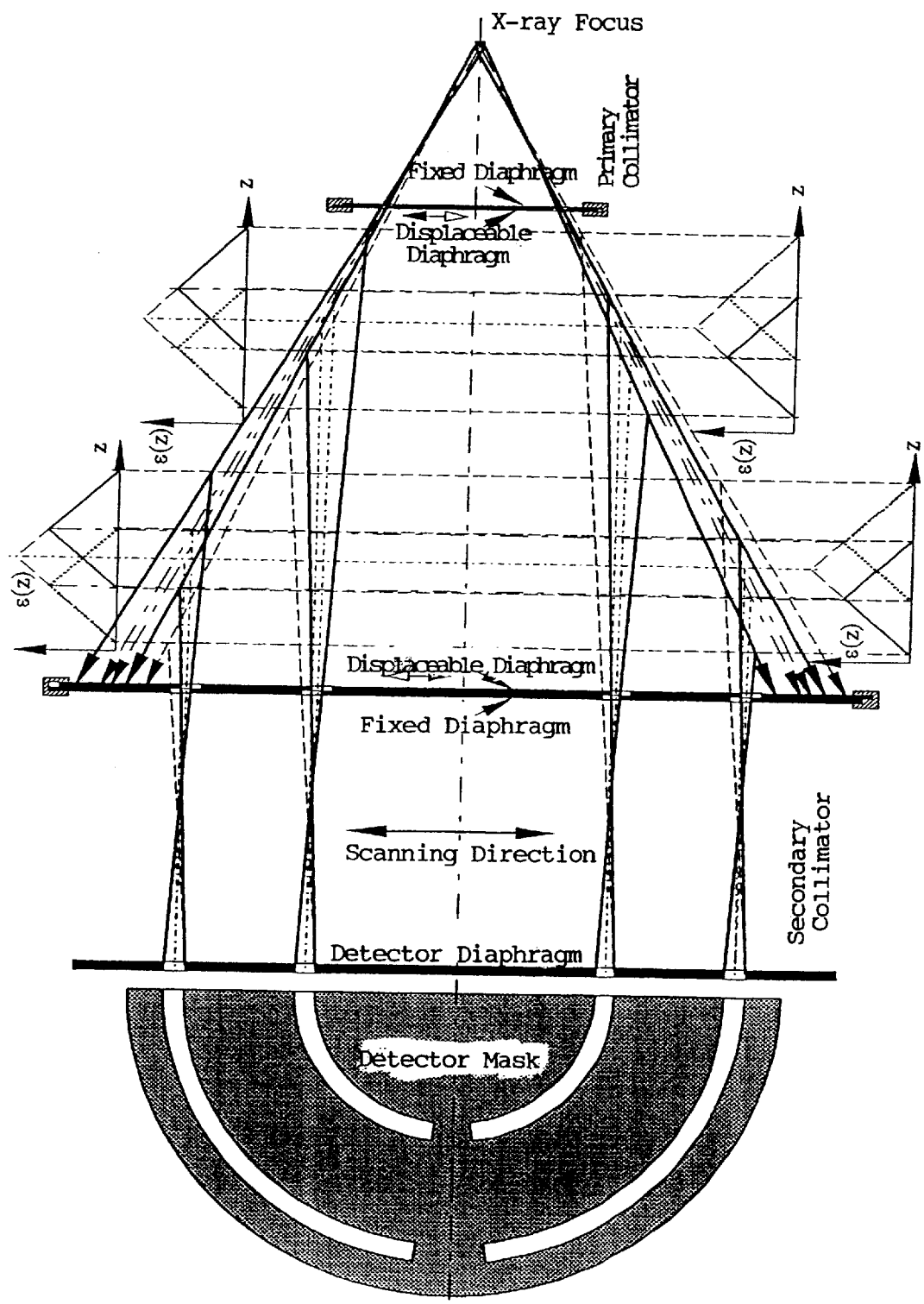
FIG. 10 is a schematic illustration of the configuration of the scattered x-ray imaging system according to the present invention with a double imaging diaphragm and a double primary collimator diaphragm; the offset of the slidable ring diaphragms is oppositely directed.

FIG. 10 shows the interaction of the pair of imaging diaphragms and the pair of primary collimator diaphragms. The slidable imaging diaphragm is moved toward the right and the slidable primary collimator diaphragm is moved to the left. The two displacements of the diaphragms in opposite directions results in vertical displacements of the imaging layers in the same direction. The displacements and the widths of the upper and lower imaging layers have become almost equal.

Figure 3:
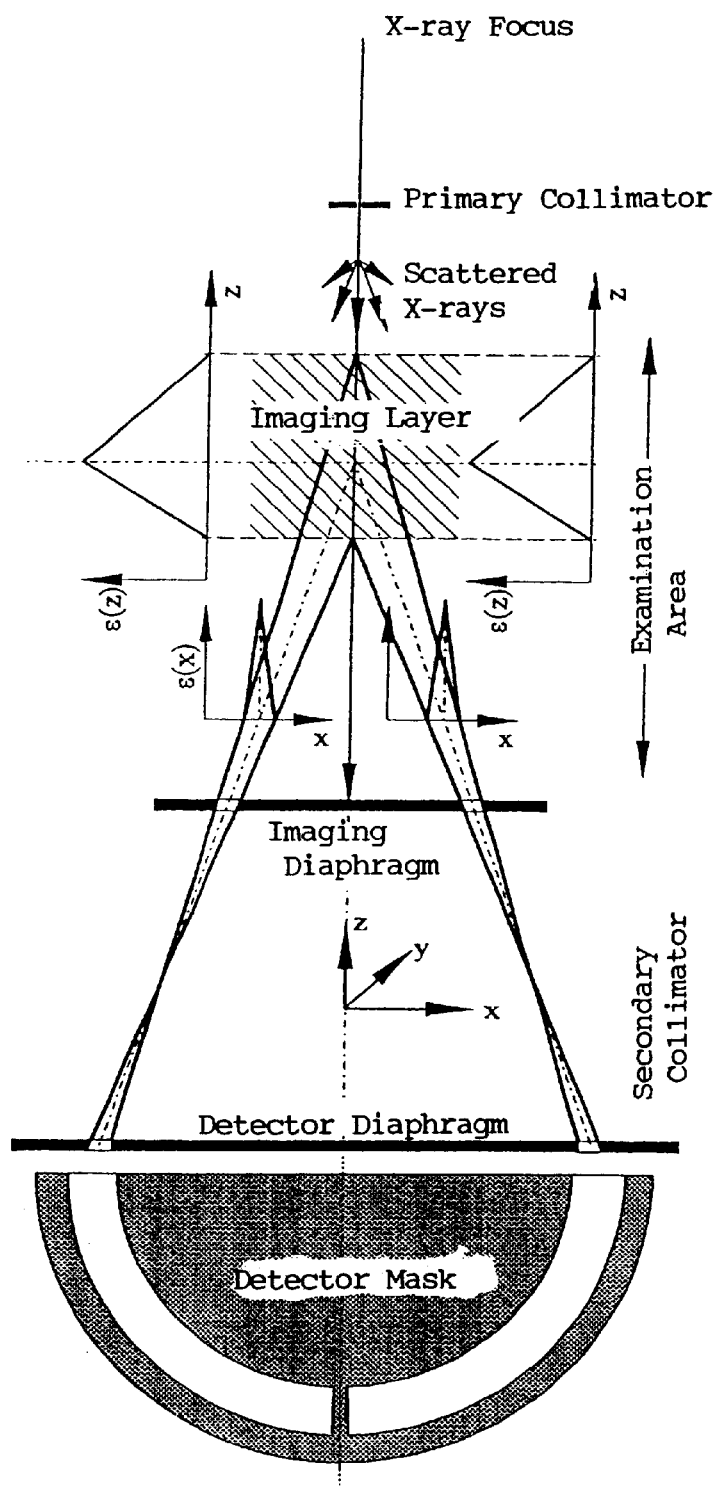
FIG. 3 is a schematic illustration of the principle of scattered x-ray imaging with a pin-shaped primary ray bundle according to the prior art.
Figure 4:
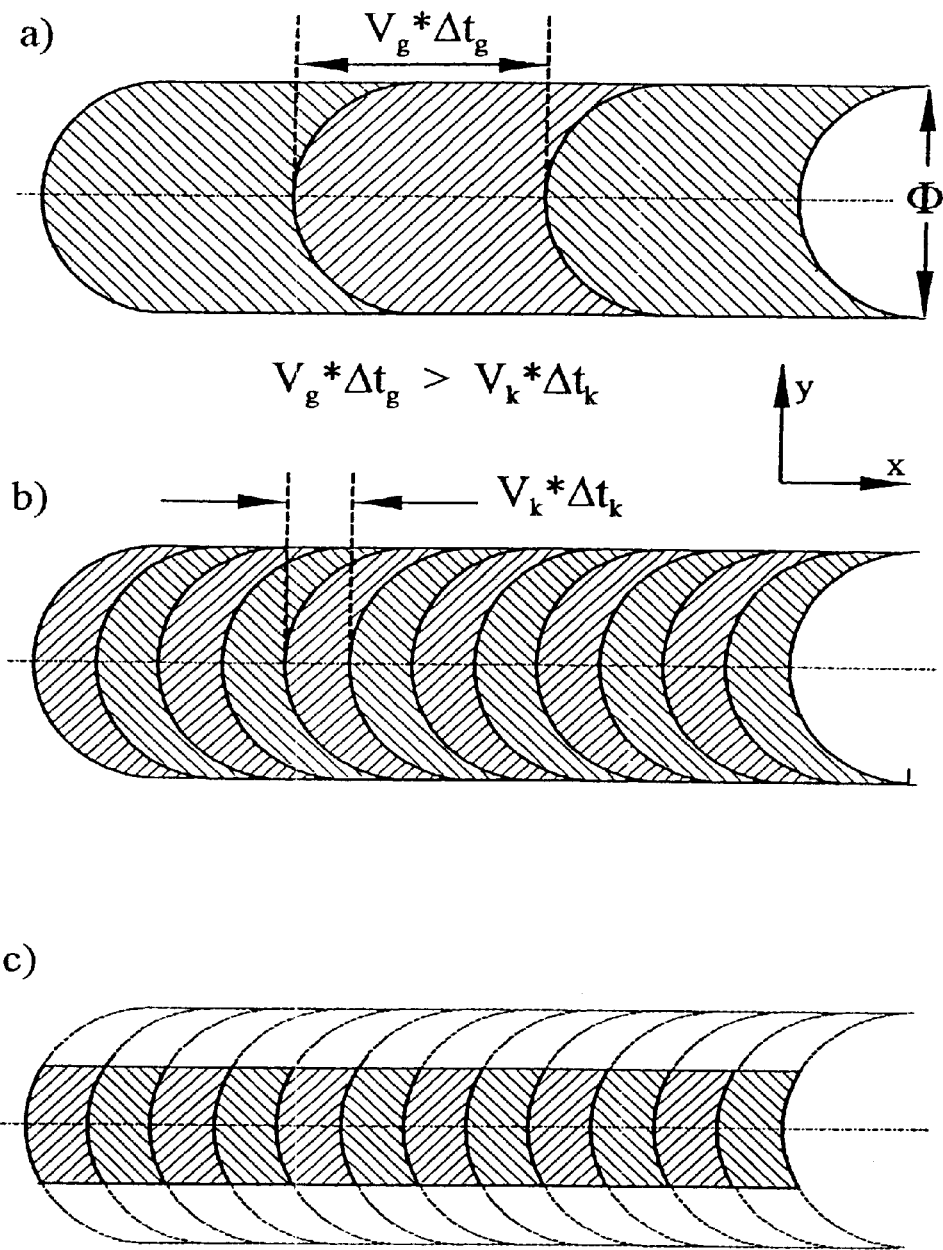
FIG. 4a shows x-y cross-sections of the "conical surface" voxels with semicircular detector structure for high scanning speeds $V_g$ and/or long integration times $\Delta t_g$.
FIG. 4b shows x-y cross-sections of the voxels for low scanning speeds $V_k$ and/or short integration times $\Delta t_k$.
FIG. 4c shows x-y cross-sections of the voxels after narrowing the ray bundle width.

Diaphragm system for vertically narrowing the "pin ray" voxel:

In a pin ray configuration as it is illustrated in FIG. 3, it is only necessary for improving the local resolution to vertically narrow the voxel in the examination space. The vertical narrowing is also in this case effected by displaceable partial diaphragms of the imaging diaphragm system. In contrast to the cone-shaped ray system, the imaging diaphragm system is not composed of one or two diaphragms with identical ring-shaped structures, but of a fixedly mounted base diaphragm having a certain ring/partial ring structure and additionally of at least three displaceable diaphragms having a ring/partial ring structure which is different from that of the base diaphragm.

When discussing the displaceable diaphragm system of the pin ray configuration, two different detector configurations or masks have to be considered.

The first detector configuration is composed of a double detector system which is divided along its diameter, as seen in FIG. 3. The second detector configuration is composed of an undivided detector.

Figure 11:
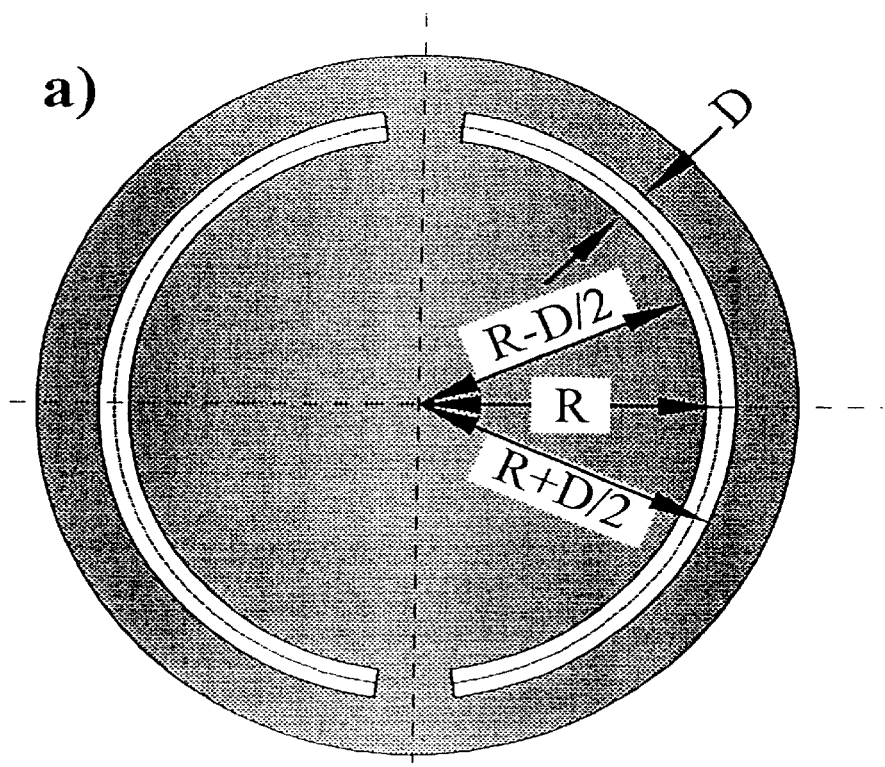
FIG. 11a is a schematic illustration of the structure of a basic diaphragm.
FIG. 11b is a schematic illustration of a slidable diaphragm for reducing the vertical voxel size in the pin ray system.
Figure 11:
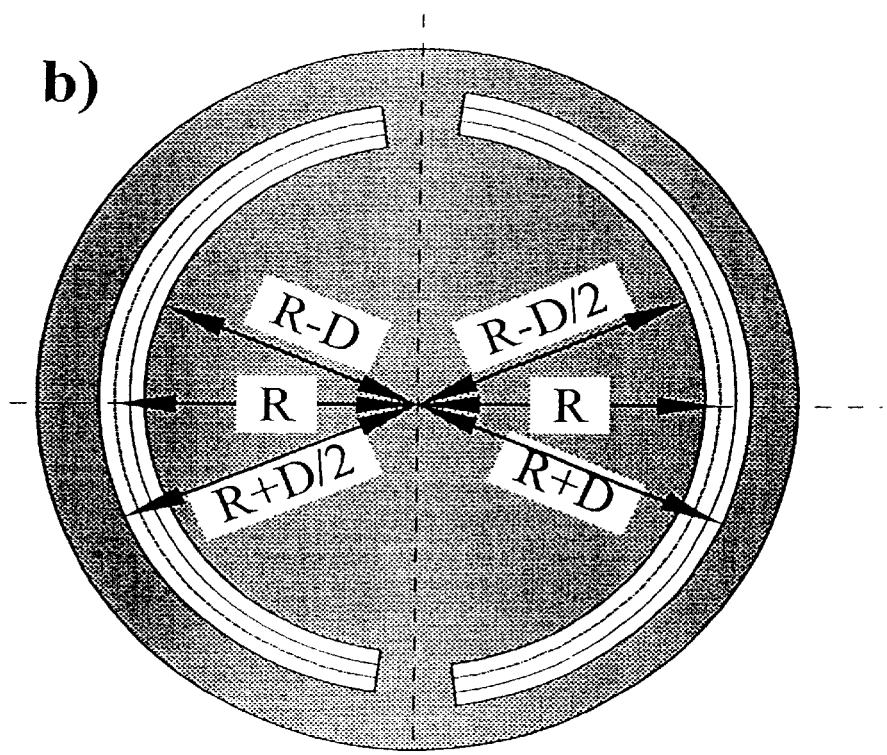

For the displaceable diaphragm system of the divided detector system, a stationary base diaphragm is used with a structure which is shown in FIG. 11a. In addition, three displaceable diaphragms having a structure shown in FIG. 11b are arranged above the base diaphragm.

Figure 12:
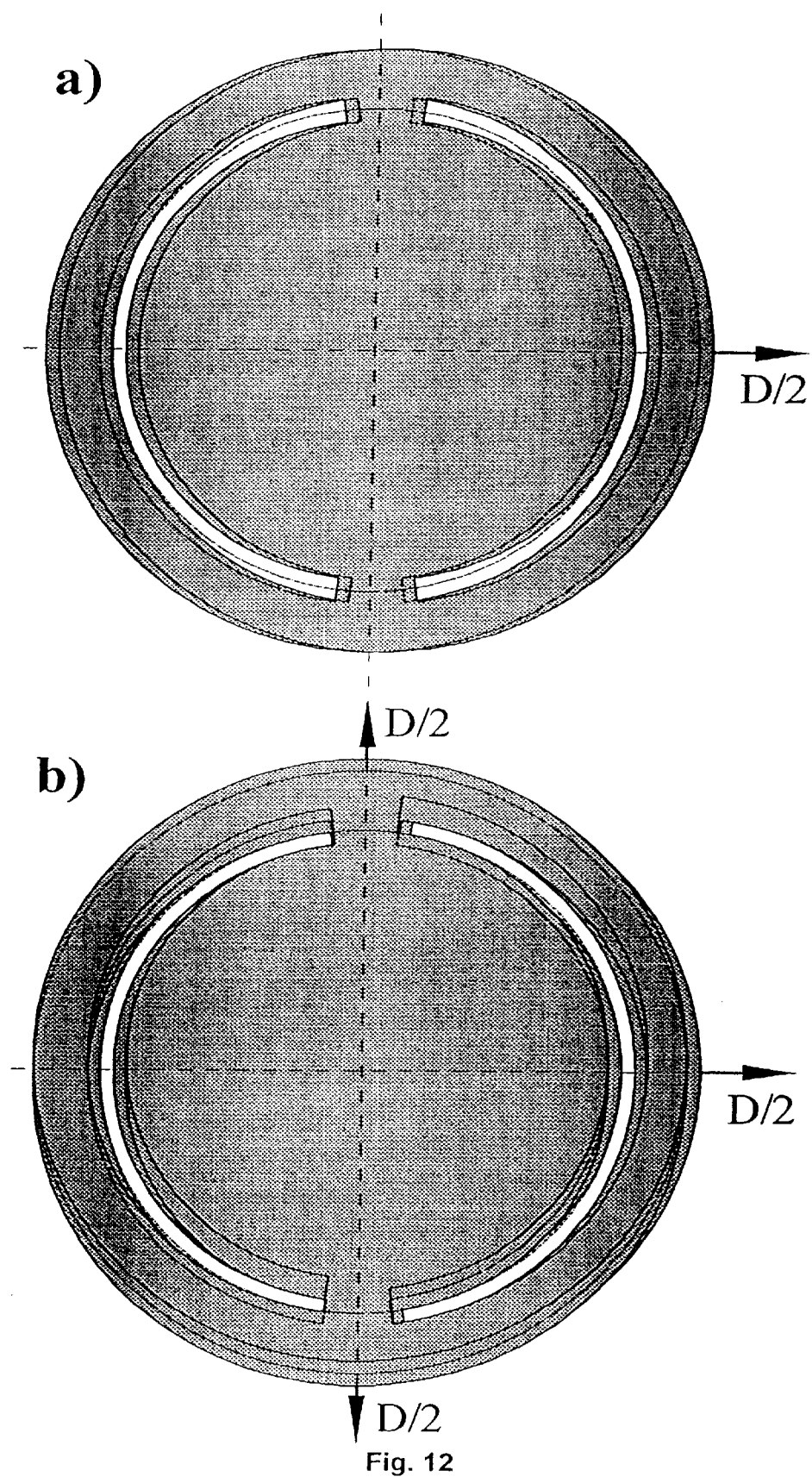

The manner of operation of this diaphragm system is illustrated in FIGS. 12a and 12b. FIG. 12a shows the base diaphragm with initially one displaceable diaphragm of the type of FIG. 11b arranged above the base diaphragm, wherein the displaceable diaphragm has been displaced toward the right by half a slot width D/2. As a result, the effective slot widths are reduced in half in the vicinity of the horizontal diameter. In the vicinity of the vertical diameter, the slot widths continue to have the size D.

By providing two additional displaceable diaphragms of the type of FIG. 11b, which are respectively moved toward the bottom and toward the top by D/2, the semicircular ring structure of FIG. 12b is obtained. In coarse approximation, the semicircular ring slots have along the entire circumference the intended half slot width of the base diaphragm. In addition, the radii of the two semicircular ring slots differ by D/2, so that the semicircular rings are offset relative to each other by D/2.

Figure 13:
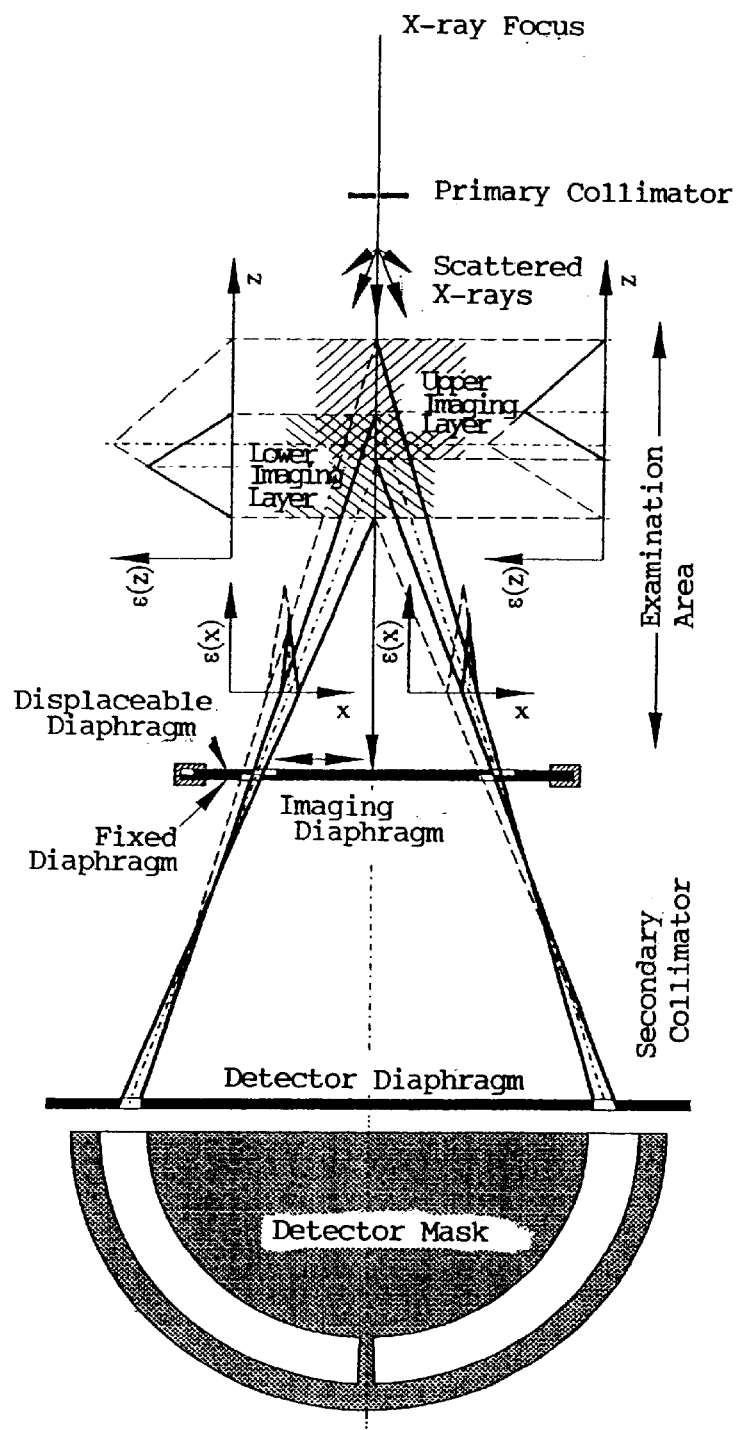
FIG. 13 is a schematic illustration showing the effect of the slidable imaging diaphragm system on the vertical voxel size and the vertical voxel position in the pin ray system with double detector.

The consequences of this effective slot reduction and effective slot displacement to the voxel size are shown in FIG. 13. The displaceable diaphragms of the imaging diaphragm system move the open area of the diaphragm system toward the right and they reduce the size of the opening. This has the result that the voxel becomes smaller and that the partial voxel on the right is moved toward the top and the partial voxel on the left is moved toward the bottom.

If the detector is constructed as described above as a divided semicircular detector or semicircular ring detector, two voxels having smaller voxel heights which are arranged above each other and partially overlap each other can then be evaluated simultaneously.

If for reasons of costs or other reasons, it is not desired to use a double detector, but an undivided detector, it is necessary for achieving the maximum signal yield to ensure that as the slot widths are reduced, the slot radia along the entire circumference of the imaging diaphragm remain the same.

Figure 14:
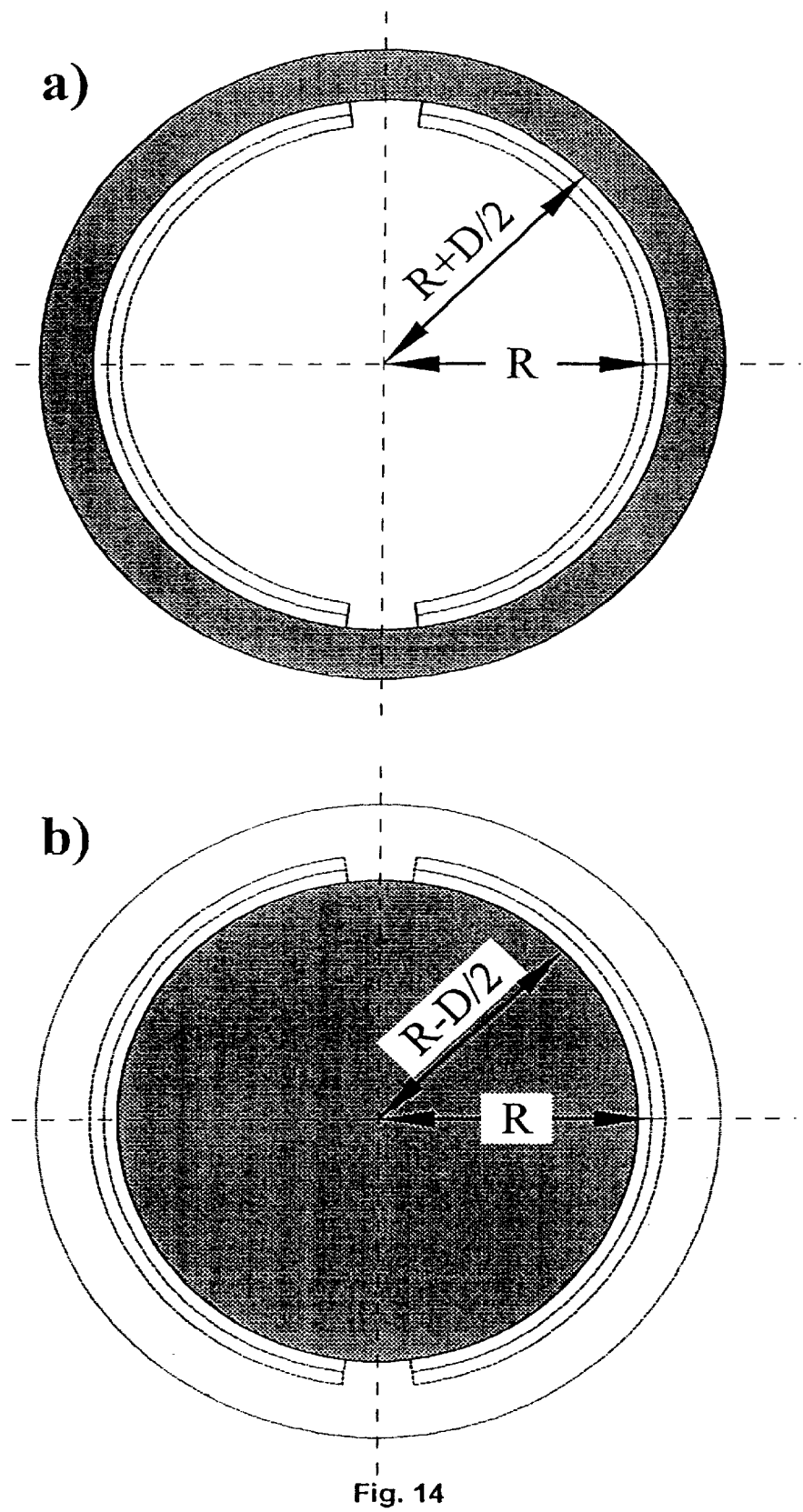
FIG. 14a is a schematic illustration of the moveable additional diaphragm for a pin ray configuration in the form of a circular ring diaphragm having an internal radius of R+D/2.
FIG. 14b is a schematic illustration of the moveable additional diaphragm for a pin ray configuration in the form of a solid circular diaphragm having an outer diameter of R−D/2.

This can be achieved by a different structure of the displaceable diaphragms. FIGS. 14a and 14b show two different types of moveable diaphragm for this case. FIG. 14a shows a circular ring diaphragm with the inner radius R+D/2, wherein R is the middle radius of the base diaphragm, as seen in FIG. 11a. FIG. 14b shows a displaceable circular diaphragm constructed as a full disc having the radius R−D/2.

Figure 15:
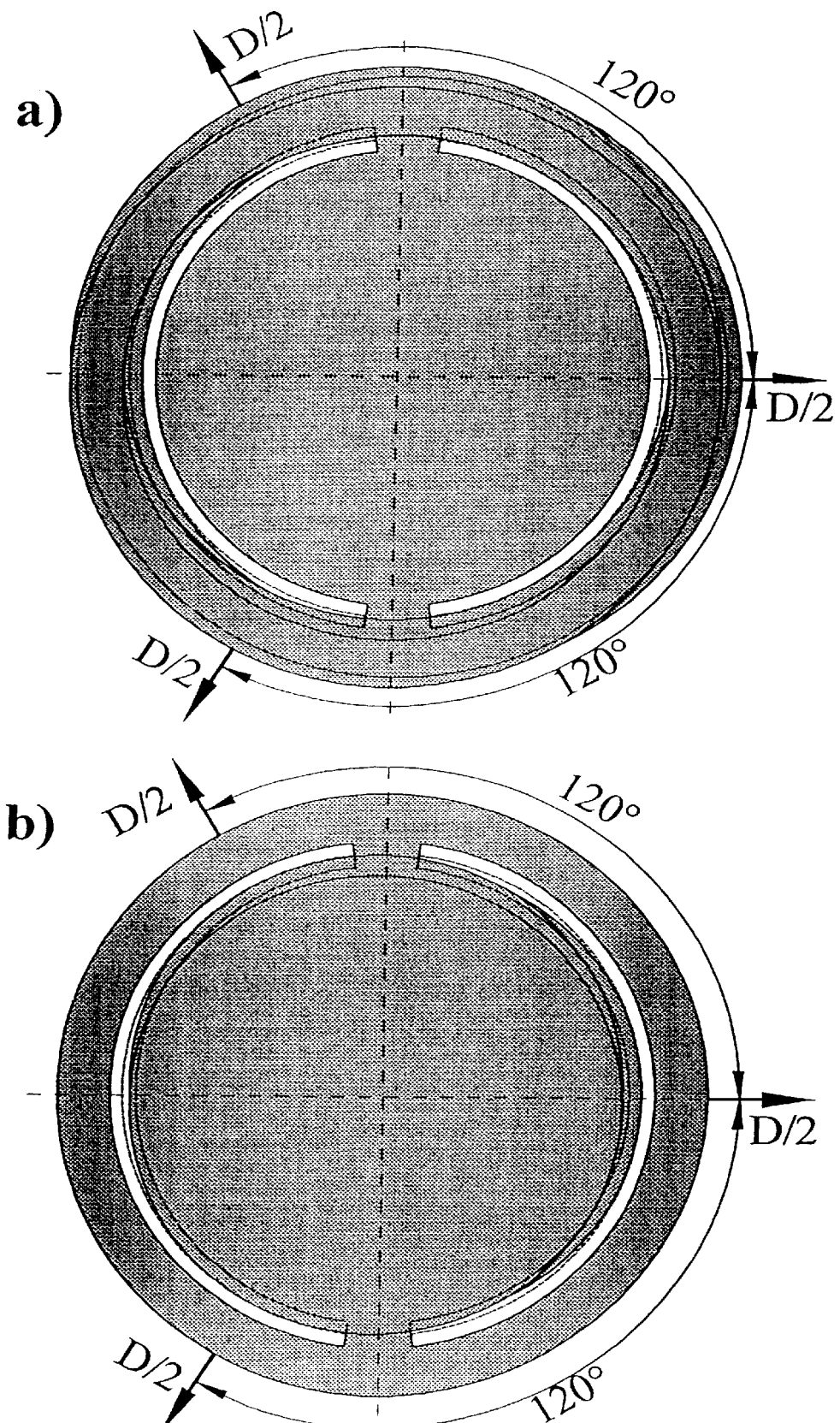
FIG. 15a is a schematic illustration of the superposition of the basic diaphragm with three circular ring diaphragms shifted outwardly by D/2 in different directions by 120°.
FIG. 15b is a schematic illustration of the superposition of the basic diaphragm with three solid circular diaphragms shifted outwardly by D/2 in different directions by 120°.

FIGS. 15a and 15b show the interaction of the circular ring diaphragm and the full diaphragm. FIG. 15a shows the effectively resulting slot distribution if the base diaphragm is superimposed with three circular ring diaphragms and one of these diaphragms is moved toward the right by D/2; the other two diaphragms are respectively moved toward the top left and toward the top right by D/2. The directions of movement relative to each other are 120°. The result is a circular ring structure with almost half the slot size as compared to that of the base diaphragm, wherein the areas remaining free correspond to the inner half of the semicircular rings of the base diaphragm.

FIG. 15b shows the effectively resulting slot distribution if the base diaphragm is superimposed with three solid diaphragms and one of these diaphragms is displaced toward the right by D/2; as is the case in FIG. 15a, the other two diaphragms are respectively moved toward the top left and toward the bottom left by D/2. The relative directions of movement are again 120°. The result is a semicircular ring structure with almost half the slot size as compared to the base diaphragm, wherein the areas remaining free correspond to the outer half of the semicircular rings of the base diaphragm.

It is apparent from FIGS. 15a and 15b that at least three displaceable additional diaphragms are necessary to obtain an almost complete semicircular ring structure with almost half the slot width. A greater perfection with respect to the slot width is obtained when using four additional diaphragms which are displaced by D/2 in four directions which are orthogonal relative to each other.

While specific embodiments of the invention have been shown and described in detail to illustrate the inventive principles, it will be understood that the invention may be embodied otherwise without departing from such principles.

I claim:

1. An apparatus for measuring a pulse transmission spectrum of elastically scattered X-ray quantities, the apparatus comprising a polychromatic x-ray emitter;

a primary diaphragm arrangement arranged between the x-ray emitter and an examination area through which x-ray radiation is conducted, wherein the primary diaphragm arrangement is configured to mask a primary ray bundle or pin ray bundle extending through the examination area on a surface of a cone;

a detector arrangement comprising several detector elements concentrically surrounding a detector center point for determining the x-ray quantities scattered in the examination area;

a secondary diaphragm arrangement arranged between the examination area and the detector arrangement, wherein the secondary diaphragm arrangement includes at least one imaging slot for imaging the scattered x-ray radiation on the detector arrangement;

a device for effecting relative displacement between an examination object placed in the examination area and the examination arrangement for scanning the examination object in a scanning direction; and means for processing measured signals, wherein the detector arrangement is divided by means of separating areas arranged perpendicularly of the scanning direction into a least two detector areas having essentially an identical width, and wherein each detector area has a number of partial ring-shaped detector elements, and each detector element has means for signal processing, further comprising a) at least one diaphragm displaceable in a y-direction for switching between fine and coarse local resolution of the examined partial volumes of the examination object, wherein the diaphragm narrows the effective ray width transversely of the scanning direction, and b) a diaphragm system displaceable in a x-direction for limiting extension of the partial volumes in a z-direction, wherein the diaphragm system includes at least two circular ring diaphragms arranged one above the other and identical with respect to their circular ring structure, wherein the circular ring diaphragms are arranged at a relative offset for reducing an effective imaging slot width or the detector slot width.

2. The apparatus according to claim 1, wherein the diaphragm displaceable in the y-direction is comprised of at least two portions and a coupling piece rigidly mechanically coupling the two portions, wherein at least one portion is arranged in a non-active state outside of the circular ring slot structure and at least one other portion is arranged within the circular ring slot structure, and wherein a displacement of the diaphragm in the y-direction in an active state results in a portion located outside of the circular ring slot to be moved inwardly for partially covering the circular ring slot, while at least another inner portion is moved outwardly and simultaneously covers an oppositely located portion of the circular ring structure.

3. The apparatus according to claim 1, comprising two separate diaphragms moveable in the y-direction for narrowing an effective ray width transversely of the scanning direction.

4. The apparatus according to claim 1, comprising at least one electromagnet for displacing the diaphragms.

5. Use of the apparatus according to claim 1 in an examination area for different quantities of crystalline substances, such as explosives and drugs contained in containers, such as pieces of luggage, packages, letters and the like.

* * * * *